United States Patent [19]

Heinzelmann et al.

[11] 4,303,830
[45] Dec. 1, 1981

[54] TOMOGRAPHIC APPARATUS FOR PRODUCING TRANSVERSE LAYER IMAGES OF A RADIOGRAPHY SUBJECT

[75] Inventors: Karl G. Heinzelmann, Neunkirchen; Güenter Schmitt, Erlangen; Edgar Tschunt, Rathsberg, all of Fed. Rep. of Germany

[73] Assignee: Siemens Aktiengesellschaft, Berlin & Munich, Fed. Rep. of Germany

[21] Appl. No.: 86,821

[22] Filed: Oct. 22, 1979

[30] Foreign Application Priority Data

Dec. 7, 1978 [DE] Fed. Rep. of Germany ....... 2852968

[51] Int. Cl.³ ............................................. G03B 41/16
[52] U.S. Cl. ................................................ 250/445 T
[58] Field of Search ............................. 250/360, 445 T

[56] References Cited
U.S. PATENT DOCUMENTS

| | | | |
|---|---|---|---|
| 4,135,095 | 1/1979 | Watanabe | 250/360 |
| 4,150,293 | 4/1979 | Franke | 250/445 T |
| 4,187,430 | 2/1980 | Schmidt | 250/445 T |
| 4,196,352 | 4/1980 | Berninger et al. | 250/445 T |
| 4,206,362 | 6/1980 | Bagby | 250/445 T |
| 4,232,226 | 11/1980 | Huettner et al. | 250/445 T |

Primary Examiner—Davis L. Willis
Attorney, Agent, or Firm—Hill, Van Santen, Steadman, Chiara & Simpson

[57] ABSTRACT

In an exemplary embodiment, several sources of radiation, arranged with their focuses angularly offset by angles of equal size, having a radiation measuring arrangement with a number of radiation receivers equal to the number of radiation sources for determining the radiation intensity behind the object, having a drive device which drives a rotating frame for producing rotational movements of the radiation sources and the radiation receivers, and also having a measured value converter for transforming the signals supplied by the radiation receivers into layer images. The radiation receivers are arranged opposite the radiation sources and are also displaced by equal angles. At least one of the measuring units each comprising a radiation source and a radiation receiver is arranged offset in the direction of the rotational axis so that the measuring units simultaneously scan a plurality of layers. This distance may be adjustable.

4 Claims, 4 Drawing Figures

TOMOGRAPHIC APPARATUS FOR PRODUCING TRANSVERSE LAYER IMAGES OF A RADIOGRAPHY SUBJECT

BACKGROUND OF THE INVENTION

The invention relates to a tomograph for producing transverse layer images of a radiography subject, having several sources of radiation, arranged with their focuses mutually offset by angles of equal size, having a radiation measuring arrangement which consists of a number of radiation receivers equal to the number of radiation sources, which determine the radiation intensity behind the subject, having a drive device which drives a rotating frame for the radiation sources and the radiation receivers, and also having a measured value converter for transforming the signals supplied by the radiation receivers into a layer image, and in which the radiation receivers are also arranged opposite the radiation sources, displaced by angles of equal size.

A tomograph of this type is described in the German Offenlegungsschrift 26 14 083 (U.S. Pat. No. 4,150,293 issued Apr. 17, 1979). In this tomograph, a computer is provided which processes the output signals of the radiation receivers, which are produced at different projections while the rotating frame is rotating, so that the radiation attenuation coefficients of specific points of the irradiated layer are calculated from them and may then be reproduced in image form. The drive device in the known tomograph is constructed so that for a scan it rotates the rotating frame by an angle which is equal to the angle of offset of the radiation sources and the radiation receivers. When there are three x-ray tubes and three radiation receivers it is necessary accordingly to rotate the rotating frame by 120°. Thus, compared with the instance where only one x-ray tube and one radiation receiver are provided the scanning time is shortened by a third.

With the known tomograph of the initially mentioned type it is only possible to scan a single layer of the radiography subject in each case. If several layers of the radiography subject are to be examined it is necessary to move the patient support longitudinally by one step after one layer has been scanned and to make another scan. As a result of alternate scanning and patient support displacement which is necessary when several layers are examined, the time taken to complete the examination of several layers is relatively long.

SUMMARY OF THE INVENTION

Proceeding from a tomograph of the initially mentioned kind, the underlying object of the invention is to effect a substantial reduction in the time taken for examining several parallel layers of the patient in a tomograph for producing cross sectional images of a patient, a so-called computer tomograph, as compared with known computer tomographs.

According to the invention, this object is achieved by arranging at least one part of the measuring units, each consisting of a radiation source and a radiation receiver, in the direction of the axis of rotation a distance apart corresponding to the desired separation of the layers to be scanned. In the case of the tomograph according to the invention, several mutually parallel layers of the radiography subject are examined by a single scanning action, i.e. by a single rotation of the rotating frame. This means that the scanning time for examining such parallel layers is substantially reduced.

A particularly advantageous further development of the invention resides in that means are present for adjusting the distance between the measuring units. This enables on the one hand the distance between examined layers to be adjusted and on the other, as the extreme case, a single layer only of the radiography subject to be scanned by all the measuring units, by means of which, as with the known tomograph described in the introduction, a shortened scanning time is obtained when compared with the use of a single measuring unit. However, in order to obtain an improved resolution, it is also possible in this case to rotate the rotating frame for a scan of the radiography subject by the same angle as that by which it is rotated if only a single measuring unit is available, if the detectors are arranged accordingly.

The invention is described in more detail in the following with reference to an exemplary embodiment represented in the accompanying sheets of drawings; and other objects, features and advantages will be apparent from this detailed disclosure and from the appended claims.

DETAILED DESCRIPTION

Figure 1:
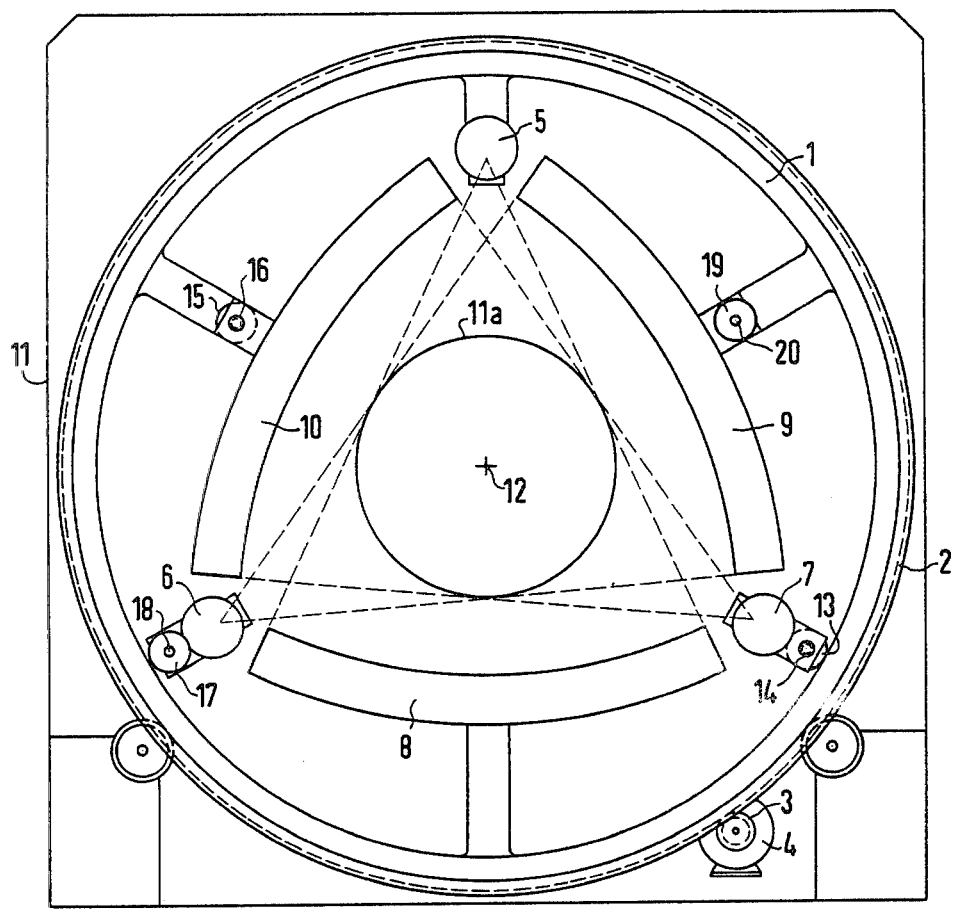
FIG. 1 shows a lateral view of a tomograph according to the invention with the housing open.
Figure 2:
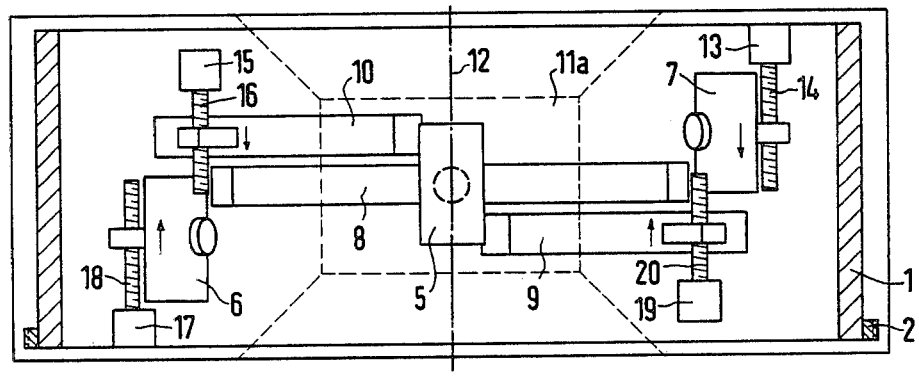
FIG. 2 shows a plan view of the unit according to FIG. 1 with a sectioned rotating frame.

FIGS. 1 and 2 show a rotating frame 1 which is constructed as a hollow cylinder and has on the outer surface of its cover a toothed wheel 2 engaging in which is a pinion 3 of a drive motor 4. Three x-ray tubes 5, 6, 7 which are mutually displaced by 120° in each case are attached to the rotating frame 1. Each of the x-ray tubes 5, 6, 7 is positioned opposite a respective radiation receiver 8, 9, 10. Each of the radiation receivers 8, 9, 10 consists of a row of detectors comprising, for example, 256 individual detectors. Each of the x-ray tubes 5, 6, 7 emits a fan-shaped beam of x-rays as indicated by the dash lines in FIG. 1. With respect to the longitudinal direction of the axis 12 of an opening 11a of the housing 11, the extent of the respective fan-shaped beams is equal to the selected thickness of the layer. The lateral extent or breadth of the respective fan-shaped beams is dimensioned so that, on the one hand, the entire opening 11a and thus the entire radiography subject is detected, while on the other hand only the associated radiation receiver is impinged by x-radiation from each x-ray source. With the patient support and patient disposed generally longitudinally of the axis 12 and within the opening 11a, the rotating frame 1 is rotated by means of the motor 4 about the axis 12. The x-ray tubes 5, 6, 7 are connected to an x-ray generator, while the radiation receivers 8, 9, 10 supply their signals to a measured value converter which forms an x-ray image from them and reproduces this on a monitor.

The x-ray tube 5 and the radiation receiver 8 are arranged in a fixed manner, i.e. they are not adjustable, on the inner cover-surface of the rotating frame 1. In contrast to this the x-ray tube 7 and the radiation receiver 10 are mounted on the rotating frame 1 so that they are adjustable in the direction of the axis of rotation 12. For this purpose a motor 13 with an adjusting spindle 14 for the x-ray tube 7 and a motor 15 with an adjusting spindle 16 for the radiation receiver 10 are mounted on the frame 1. In the same way, the measuring unit, consisting of the x-ray tube 6 and the radiation receiver 9, is adjustable in the direction of the rotation axis 12 by means of a motor 17, fixed on the rotating frame 1, with an adjusting spindle 18 for the x-ray tube 6 and a motor 19, similarly fixed on the rotating frame 1, with an adjusting spindle 20 for the radiation receiver 9.

By means of adjusting the measuring units 6, 9 and 7, 10 in the direction of the rotation axis 12, the distance of these measuring units from the measuring unit 5, 8 can be determined and thus a spacing can be selected corresponding to the spacing of three parallel body layers which can be scanned simultaneously e.g. by one complete 360° rotation of the rotating frame 1. However, it is also possible to adjust the measuring units 6, 9 and 7, 10 so that all three measuring units 5, 8; 6, 9; 7, 10 lie in one plane. In this case, only a rotation of 120° need be effected for the same image resolution as that obtained when the measuring units are arranged a distance apart and rotated through 360°. The time taken for scanning a layer is therefore only a third of the time required for scanning a layer with the measuring units offset longitudinally from one another according to FIG. 2. If, when the measuring units are located in one plane, the scanning angle selected is greater than 120°, e.g. 360°, then, with a suitable formation of the radiation receivers 8, 9, 10, i.e. with a suitable arrangement of the individual detectors, a greater number of output signals is produced per layer than when the measuring units are longitudinally offset from one another. This produces a better image resolution.

Figure 3:
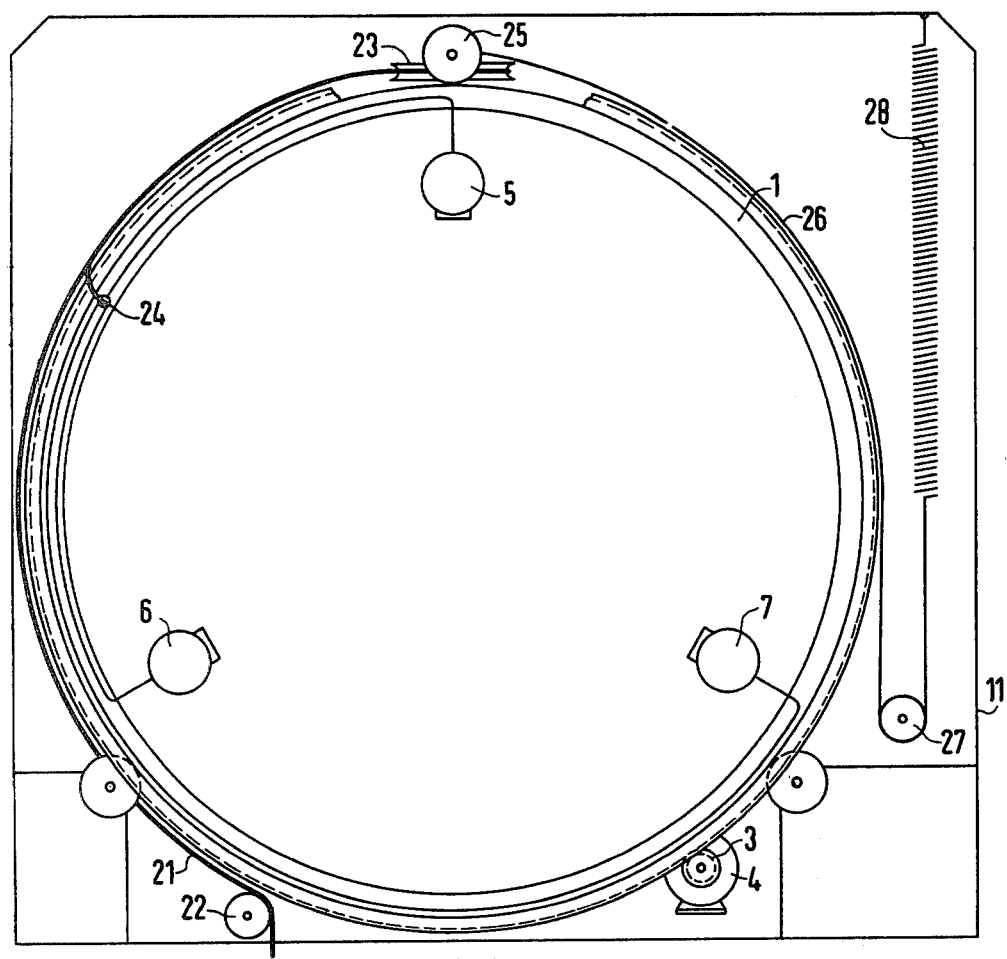
FIG. 3 shows a schematic view of the unit according to FIG. 1 to illustrate the way in which the cables for the radiation sources are guided.
Figure 4:
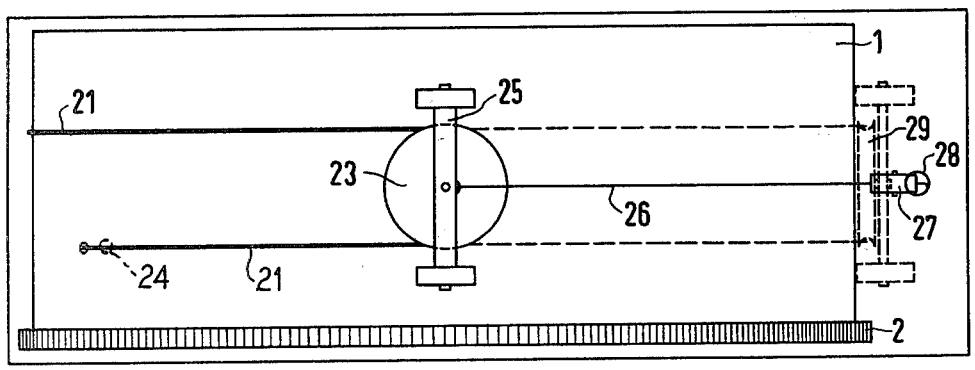
FIG. 4 shows a view from above of the cable-guiding according to FIG. 3.

In accordance with FIGS. 3 and 4, showing only those parts which are essential for the supply, the high voltage and if necessary the control signals are supplied to the x-ray tubes 5, 6, 7 by cables 21 coming from the x-ray generator, which are conducted via a roller 22 arranged in the base of the unit and laid around the outer cover of the rotating frame 1. From the roller 22 the cables are conducted to a roller 23 on the cover of the rotating frame 1 and from there to a fixed point 24 of the rotating frame 1. A fixed cabling leads from the point 24 to the x-ray tubes 5, 6, 7. The roller 23 is displaceable on the cover of the rotating frame 1 in the peripheral direction by means of a carriage 25. Engaging with this is a cable line 26 which is guided via a roller 27, which is mounted on a stationary part of the unit, and is attached to a spring 28 which is secured at one end to the housing 11.

When the rotating frame 1 rotates the roller 23 is guided by carriage 25 to move along the periphery of the cover of the rotating track 1 and holds the cable 21 taut. Thus, the roller 23 moves, for example, into the position drawn in broken lines in FIG. 4 and shown by the reference numeral 29.

By way of example, with the adjustment means 13–20 actuated to place all the sources 5, 6, 7 and receivers 8, 9, 10 in a common plane, increased resolution may be obtained in scanning a single layer if the detector units of each receiver 8, 9, 10 have a common interval or separation but are respectively offset by one-third of such common interval. Thus if there are 256 detector units per receiver and each source is pulsed once per degree of rotation of the frame 1, the total number of different projections will be three times the product of 256 and 360 (rather than being three sets of readings for each of 256×360 projections).

For the cases where the frame 1 is to be adapted for rotation through 360°, the frame 1 may initially be in a position displaced 180° counterclockwise from the position shown in FIG. 3 in which case carriage 25 will be displaced by 90° in the counterclockwise direction. The length of cable line 26 and spring 28, which are only diagrammatically indicated, must of course be sufficient to accommodate such an initial position of the carriage. (For example the pulley 27 may be mounted at a lower lever, and/or the spring 28 may extend diagonally so that its lower end has the necessary spacing from pulley 27 which may be suitably canted.) In the course of a 360° rotation of the frame 1 in the clockwise direction from such an initial position, the carriage 25 will move clockwise through 180° to the position indicated in dash outline in FIG. 4 with the pulley 23 at position 29 and the spring 28 constricted to hold cable line 26 taut.

It will be apparent that many modifications and variations may be effected without departing from the scope of the novel concepts and teachings of the present invention.

We claim as our invention:

1. A tomographic apparatus for producing transverse layer images of a radiography subject, having measuring units comprising several sources of radiation arranged with their focuses angularly offset by angles of equal size, and a radiation measuring arrangement which comprises radiation receivers for determining the radiation intensity behind the subject, having a drive device which drives a rotating frame for the radiation sources so as to rotate the radiation sources about an axis of rotation (12), and also having a measured value converter for transforming the signals supplied by the radiation receivers into layer images, at least one radiation source and radiation receiver (6, 9; 7, 10) of the measuring units (5, 8; 6, 9; 7, 10) being arranged offset in the direction of the axis of rotation (12) relative to another of the measuring units, and means comprising the offset arrangement of the measuring units for effecting the simultaneously scanning of a plurality of layers during rotation of said rotating frame about the axis of rotation (12), characterized in that, adjusting means (13 to 20) are provided for adjusting the axial distance between the measuring units (5, 8; 6, 9; 7, 10), measured parallel to said axis of rotation (12).

2. A tomographic apparatus according to claim 1 with said adjusting means providing for the selective scanning of a single layer during a given angular travel of the rotating frame which is a fraction of the angular travel required for the simultaneous generation of a plurality of layer images.

3. A tomographic apparatus according to claim 1 with said adjusting means selectively providing for the scanning of three layers during a given angular travel of the rotating frame, and alternatively selectively providing for the scanning of a single layer with increased resolution during the same angular travel of the rotating frame.

4. A tomographic apparatus according to claim 1, with said adjusting means comprising electromotors (13, 15, 17, 19) coupled with respective sources and radiation receivers and operable to move at least two sources (6, 7) and two radiation receivers (9, 10) in an axial direction while a third source (5) and a third radiation receiver (8) remain stationary with respect to said axial direction, so as to provide for the simultaneous scanning of three parallel body layers of adjustable spacing from each other.

* * * * *